United States Patent [19]
Drzewiecki

[11] 4,328,699
[45] May 11, 1982

[54] FLUERIC DENSITY AND FORCE SENSOR
[75] Inventor: Tadeusz M. Drzewiecki, Silver Spring, Md.
[73] Assignee: The United States of America as represented by the Secretary of the Army, Washington, D.C.
[21] Appl. No.: 161,793
[22] Filed: Jun. 23, 1980
[51] Int. Cl.³ .................... G01N 9/00; G01P 15/03
[52] U.S. Cl. ........................... 73/30; 73/515; 137/806
[58] Field of Search ............... 73/515, 516 LM, 32 R, 73/54, 23, 30; 137/804–806, 822–824, 827, 834

[56] References Cited
U.S. PATENT DOCUMENTS 3,205,715  9/1965  Meek ............................ 73/516 LM
3,592,042  7/1971  Martinez ........................... 73/23
3,654,944  4/1972  Laakaniemi ....................... 137/823
3,765,224 10/1973  Ostdiek ............................ 73/32 R
3,952,576  4/1976  Drzewiecki et al. ................. 73/54

Primary Examiner—James J. Gill
Attorney, Agent, or Firm—Nathan Edelberg; Robert P. Gibson; Saul Elbaum

[57] ABSTRACT

Density of a sample or its concentration are sensed by a fluidic device having a nozzle with a divider for emitting the sample and a reference fluid as layers of a single laminar jet. The deflection of the jet in a fixed force field is sensed as an indicator of density or concentration. The same device can measure acceleration transverse to the nozzle axis or attitude in a fixed force field as a function of sensed jet deflection. The sensitivity of the acceleration and attitude sensor is a function of the density of the two selected fluids used in the layered laminar jet.

7 Claims, 5 Drawing Figures

SAMPLE DENSER THAN REFERENCE

SAMPLE LESS DENSE THAN REFERENCE $a > g$

FLUERIC DENSITY AND FORCE SENSOR

RIGHTS OF THE GOVERNMENT

The invention described herein may be manufactured, used and licensed by or for the United States government for governmental purposes without the payment to me of any royalties thereon.

BACKGROUND OF THE INVENTION

The present invention relates generally to analog flueric devices and more specifically to a flueric device which is capable of being used as a density concentration, acceleration and attitude sensor.

There are numerous ways to sense the concentration of one fluid in another, fluidically. These methods are categorized by the acutal physical property that they utilize for inferring the concentration. There are essentially three properties that fluidics exploits to sense the difference between an unknown gas/fluid and a reference: (1) viscosity, (2) ratio of specific heats, and (3) density.

Patents covering the use of these three properties or combination thereof abound. Viscosity is used by Drzewiecki and Manion in U.S. Pat. No. 3,952,576. When a change in fluid viscosity is affected in one control channel of a fluidic proportional amplifier and not in the other, the jet in the amplifier is caused to deflect due to a difference in flows hence a signal output is realized as a function of difference in viscosity which can be directly related to the concentration of a known gas/fluid in another.

Viscosity and density are used in combination in the orifice-capillary bridge concentration sensor as shown in U.S. Pat. No. 3,771,348 to Villarroel. Changes in both density and viscosity produce changes in resistance. The orifice resistance is a function of density, and the capillary resistance is a function of viscosity. The pressure between the orifice and capillary changes according to these parameters and when compared with a reference orifice/capillary pair produces a differential pressure that is a function of concentration.

The ratio of specific heats determines the speed of sound through a medium. Cavity oscillators, edge tone oscillators and feedback oscillators, all have frequencies that are dependent on the speed of sound. As changes of concentration occur, the frequency of operation changes, and this change can be directly relative to the concentration. An example of using an oscillator to determine concentration is illustrated in U.S. Pat. No. 3,756,068 to Villarroel and Joyce.

Lastly, but certainly not inclusively, density or relative weight in a force/acceleration field is used in vortex concentration sensors illustrated in U.S. Pat. No. 3,765,224 to Ostdiek and Manion. The vortex device utilizes a radial flow field where a reference gas and an unknown gas are admitted on the two semicircular sides of a radial flow, the line of separation being vertical or inline with the gravitational field. When a denser (heavier) fluid is introduced on one side, a weak vortex is formed since the heavy gas at the top falls on the lighter and the lighter fluid rises through the heavy one. This weak vortex can be detected by angle of attack sensors and is capable of sensing concentrations, say of $CO_2$ in $N_2$, of less than 1 ppm. The main problem with this device is it has an extremely high output impedance. As with the vortex rate sensor, the sensitivity is greatly degraded (by the ratio of input-to-output impedance) when loaded into a fluidic system. This degradation is often of the order of 100 and more. Thus, there exists a need for an improved density type flueric concentration sensor with low output impedance.

Flueric laminar jet linear accelerometers are well known. A flueric laminar jet accelerometer is illustrated in U.S. Pat. No. 3,971,257 to Drzewiecki. A laminar jet stream is emitted from a nozzle into a chamber vented to an ambient environment. A pair of fluidic output sensors are disposed downstream of the vented chamber symmetrically about the center axis of the laminar jet stream to monitor deflection of the jet stream in an applied force field and provide a differential output as an indication of the deflection and applied force field. Although being an improvement over prior laminar jet accelerometers, the flueric laminar jet linear accelerometer of U.S. Pat. No. 3,971,257 is a very insensitive device and requires acceleration fields of a thousand times gravity to obtain a sensed reading. In spite of this limitation, the flueric accelerometer has a very low output impedance that is readily interfaced with other fluidic devices and circuits. Thus, there exists a need for a flueric laminar jet linear accelerometer which maintains its low output impedance with the greater sensitivity.

SUMMARY OF THE INVENTION

An object of the present invention is to provide a concentration sensor having low output impendance.

Another object of the invention is to provide a flueric density sensor with low output impendance.

A further object of the invention is to provide a flueric laminar jet accelerometer with improved sensitivity.

Still another object of the present invention is to provide a laminar jet attitude sensor with improved sensitivity.

A still even further object of the present invention is to provide a flueric sensor which is capable of detecting concentration, density, acceleration, and attitude.

These and other objects are attained by modifying the laminar jet accelerometer disclosed in U.S. Pat. No. 3,971,257 to provide a composite laminar jet having a first and second fluid layer. For use as a concentration or density sensor, a first fluid or reference fluid is applied on one side of a divider in the nozzle which creates the jet with the sample being provided on the other side of the divider. The deflection of the composited jet in a fixed acceleration field is monitored by a pair of symmetrical output channels. To draw samples into the chamber between the nozzle and the output channels, the vents of the chamber are at a negative pressure compared to the sources. Since the sensors are modifications of the laminar jet accelerometer, it retains the low output impedance of the laminar jet accelerometer. The sensor may also be used as an accelerometer with increased sensitivity. The composite jet is selected to be formed from two fluids of a known differential density which defines the sensitivity of the accelerometer. The acceleration forces applied traverse to the axis of the jet will deflect it and the output channels will indicate the deflection of the jet as an indication of acceleration. In a fixed acceleration field, the deflection of the composite jet will reflect the attitude of the jet centerline relative to the horizontal. The difference in density of the two layers which form the composite jet will determine the sensitivity of the sensor.

Other objects, advantages and novel features of the present invention will become apparent from the following detailed description of the invention when considered in conjunction with the accompanying drawings.

DESCRIPTION OF THE PREFERRED EMBODIMENT

Before beginning the detailed description of the apparatus of the present invention, it should be noted that the word "flueric" is a known word of art which specifically refers to a purely fluid element, that is, one having no moving parts and thus no chance for breakdown or failure. In contradistinction, the words "fluidic" or "fluid" are much broader than the term "flueric" and are known in the art to refer to any type of fluid element, such as those having diaphragms, pistons, and similar moving parts. These known definitions of words "fluid," "fluidic" and "flueric" are further exemplified by reference to the Military Standard Fluidics Terminology and Symbols Textbook, dated July 17, 1968, and generally referred to as "MIL-STD-1306." This document is an official Department of Defense publication.

Figure 1:
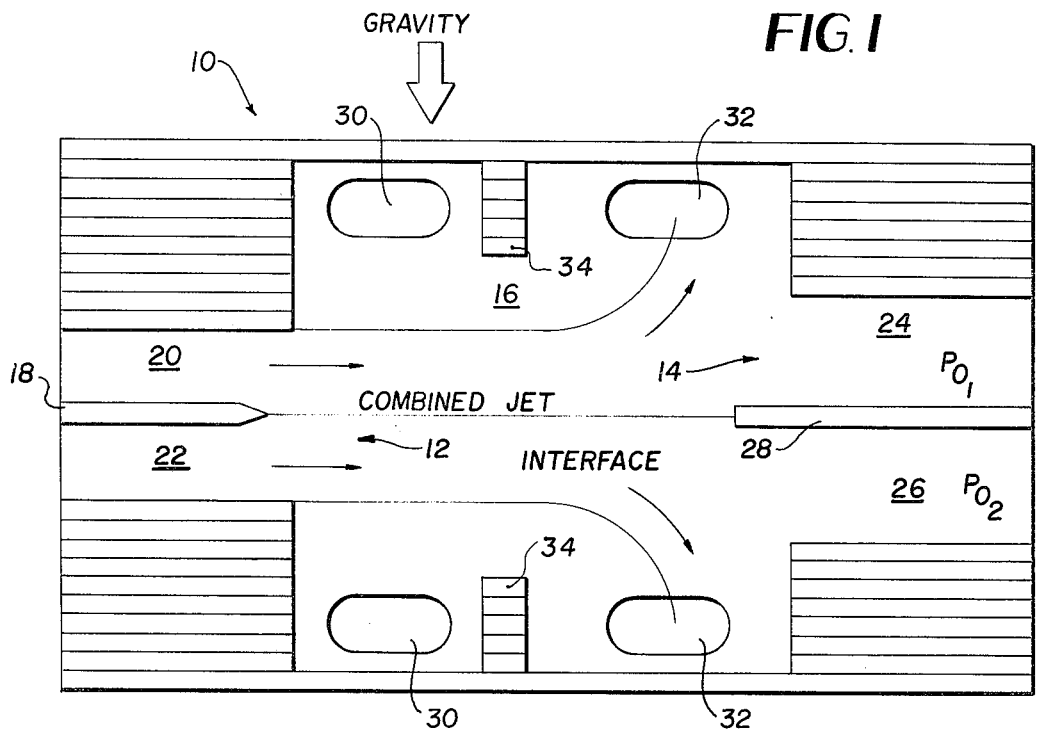
FIG. 1 is a crossectional view of a flueric sensor incorporating the principles of the present invention.

A flueric laminar flow sensor 10 as illustrated in FIG. 1, includes the nozzle 12 which emits the jet received and monitored by an output 14. The nozzle 12 and output 14 are connected by a deflection chamber 16. The nozzle 12 includes a divider 18 to define a first fluid section 20 for a sample fluid and a second fluid portion channel 22 for the reference fluid. The composite jet emitted from the nozzle 12 is a substantially heterogeneous, two layered jet having the sample on the top and the reference fluid on the bottom thereof. The output means 14 includes a first outlet channel 24 and a second outlet channel 26 symmetrical about the center axis of the composite jet and separated by splitter 28. The pressure outputs PO1 and PO2 of output channels 24 and 26 are indications of the direction and amount of deflection of the composite jet. The deflection chamber 16 includes a first pair of vents 30 on opposite sides of the composite jet adjacent the nozzle 12 and a second pair of vents 32 on opposite sides of the composite jet and adjacent to the output means 14. By the application of a negative pressure or a vacuum to the vents 30 and 32, the reference and sample fluids may be drawn into deflection chamber 16. Vanes 34 separate vents 30 from 32 to prevent the jet fluid not received by output 14 from being recirculated back toward the nozzle 12.

As is evident from FIG. 1, the flueric laminar jet sensor 10 of FIG. 1 is substantially the same configuration as the laminar jet linear accelerometer of U.S. Pat. No. 3,971,257. The major difference being that the nozzle 12 is separated into two halves by divider 18. The sensor 10 is illustrated as being formed from a plurality of vertical laminations. Thus, the only two modifications to the laminar jet linear accelerometer would be to (a) replace the splitter lamination of the output with a new splitter which includes not only splitter 28 at the output but the divider 18 at the input or nozzle section 12 and (b) provide two input parts for the two fluids. Although sensor 10 is shown as being made of a plurality of vertical laminations, it is obvious that the sensor of the present invention may be formed using other flueric technology. By using the laminar jet linear accelerometer configuration, the low output impedance is maintained.

Figure 2:
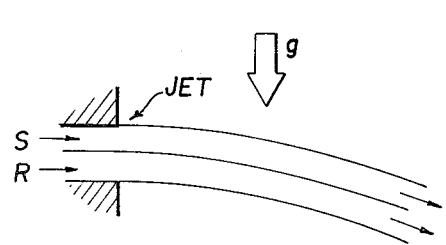
FIG. 2 is a schematic presentation of the jet wherein the sample layer is denser than the reference layer.
Figure 3:
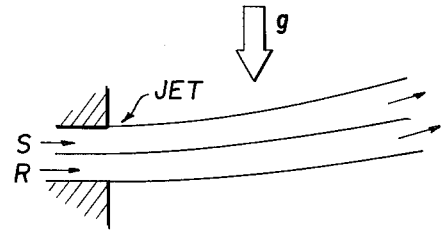
FIG. 3 is a schematic representation of a jet wherein the sample layer is less dense than the reference layer.

Flueric laminar jet sensor 10 may be used as a density type of concentration sensor. If the sample fluid S has a greater density than the reference fluid R in a fixed force field, for example, a gravity, the composite laminar jet stream will deflect downward as illustrated in FIG. 2. Conversely, if the sample fluid S, which represents the top layer of the laminar jet, is of a less density than the reference fluid R which forms the lower layer of the laminar jet, the composite laminar jet will deflect upward as illustrated in FIG. 3. In response to the downward or upward deflection of FIGS. 2 or 3, the output pressures PO1 and PO2 will become unbalanced and thus the difference in pressure is a measure of the difference in density and conversely the difference in density will deflect the difference in composition between the sample fluid S and the reference fluid R. It should be noted that placing the sample fluid on top and the reference fluid on the bottom is merely an example and the relative positions may be reversed.

If one assumes that for a typical laminar fluidic device, a jet deflection can be sensed that is $10^{-6}$ of the saturated jet deflection, then a threshold difference in density can be estimated. The saturation deflection occurs approximately when the jet has moved half a nozzle width at the output. From "Analytical Design of Laminar Proportional Amplifiers," Manion and Drzewiecki, Proc HDL Fluidic State-of-the-Art Symposium, 1974, Vol. I, the jet deflection, $\delta$, by pressure, $\Delta P_j$, is $$\frac{\delta}{b_s} = \frac{B_c^2 \Delta P_j}{4 C_\theta P_s}$$

where
$B_c$ = distance over which pressure acts divided by the nozzle width $b_s$
$b_s$ = nozzle width
$C_\theta$ = momentum flux discharge coefficient = 1.32 $c_d^2$ where $c_d$ is discharge coefficient of nozzle.
$P_s$ = supply pressure to vent pressure differential.

If one assumes no mixing of the two streams (this holds true if the transport time is less than the diffusion time), then the differential pressure caused by a difference in density is simply $$\Delta P = \frac{\Delta \text{FORCE}}{\text{AREA}} = \frac{\Delta \zeta b_s}{2} \frac{b_c hg}{b_c h} = \frac{b_s g \Delta \zeta}{2}$$

where one notes that $\Delta F = \Delta(\text{mass}) \times \text{acceleration} = \Delta(\text{density}) \times \text{volume} \times \text{acceleration}$, and area = length × height, ($b_c h$).

If $\delta/b_s = 0.5 \times 10^{-6}$,
and substituting equation (2) into equation (1), then the difference in density becomes $$\frac{\Delta \zeta|}{\min} = \frac{4C_\theta P_s}{B_c^2 b_s g} \times 10^{-6} = 80 \times 10^{-6} \text{ kg/m}^3 \quad (3)$$

For the typical values of $C_\theta = 0.4$ $P_s = 100$ pa (kg/ms$^2$) (air)

$B_c = 20$ $b_s = 0.5 \times 10^{-3}$ m $g = 10$ m/s$^2$ $\xi = 1.2059$ kg/m$^3$ (air)

Figure 4:
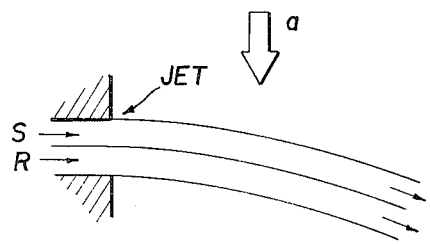
FIG. 4 is a schematic representation of the jet deflecting in response to an acceleration greater than gravity at a fixed differential density of the two fluids of the jet.

The flueric sensor 10 of FIG. 1 may also be used to monitor acceleration forces transverse to the axis of the composite jet. An examination of equation (2) will indicate that the differential pressure at the output channels can also be a function of the acceleration field wherein the term "g" for gravity becomes "a" for acceleration. Thus for a fixed differential in density ($\Delta \zeta$) the change in pressure is directly related to the acceleration force. By selecting the differential of density ($\Delta \zeta$) between the two fluids S and R which form the composite jet, the sensitivity of device 10 or the differential pressures monitored can be varied. Thus the device may be designed for extremely low or extremely high accelerations depending upon the differential of density of the fluids S and R. The deflection of the composite laminar jet in response to an acceleration greater than gravity is illustrated in FIG. 4.

Figure 5:
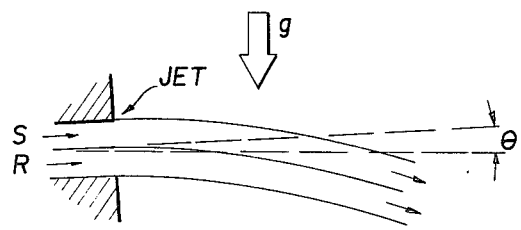
FIG. 5 is a schematic representation of the jet at a fixed acceleration functioning as an attitude sensor.

Using the same philosophy, the device 10 may be used to indicate the attitude of the device. As illustrated in FIG. 5, the flueric device 10 may be rotated such that the centerline of the nozzle 12 is set at an angle ($\theta$) relative to the horizontal. For the fixed gravitational field transverse to the horizontal, the composite jet will deflect as illustrated in FIG. 5. The differential output pressure then becomes a function of the angle ($\theta$) and equation (2) becomes $$\Delta P = \frac{b_s \Delta \zeta g}{2} \cos \theta \quad (4)$$

As with the accelerometer, the sensitivity of the sensor 10 may be adjusted by varying the differential density of the fluids S and R.

Thus, the flueric sensor 10 can measure either fluid density or concentration relative to a reference, attitude relative to a gravitational field, and linear or angular acceleration when that acceleration is perpendicular to the jet axis. The device is an improvement over other devices in that it inherently consumes less flow than vortex devices, has an inherently low output impedance (it has the output impedance of an amplifier) as compared to a bridge or a vortex sensor, has considerably more sensitivity than the other devices when staged in a control system, and has at least as good a potential for extremely low resolution as does the vortex device but at considerably faster response since the response is limited by the relatively fast transport time between nozzle and output; whereas, the vortex device is limited by the fill time which for a similar sensitivity is considerably longer. The device is simple to manufacture since it requires only the alteration of one laminate (the central one) of an existing laminar jet rate sensor (LJARS).

From the preceding description of the preferred embodiments, it is evident that the objects of the invention are attained and although the invention has been described and illustrated in detail it is to be clearly understood that the same is by way of illustration and example only and is not to be taken by way of limitation. The spirit and scope of this invention are to be limited only by the terms of the appended claims.

I wish it to be understood that I do not desire to be limited to the exact details of constructions shown and described, for obvious modifications can be made by persons skilled in the art.

What is claimed:

1. A laminar flueric density sensor comprising:
   a nozzle with a divider for emitting a sample fluid and a reference fluid from a respective side of said divider as a single laminar jet;
   sensing means disposed downstream for sensing deflection of said jet about the nozzle's centerline as an indication of relative density of said sample fluid and said reference fluid; and
   a chamber interconnecting said nozzle and said sensing means for accommodating deflection of said jet.

2. The laminar flueric density sensor according to claim 1 wherein said sensing means includes a pair of output channels symmetrical about a divider which is on said centerline.

3. A laminar flueric accelerometer comprising:
   a nozzle with a divider for emitting a first and second fluid from respective sides of said divider said first and second fluid forming adjacent streams into a single laminar jet;
   sensing means disposed downstream and symmetrically about the centerline of said nozzle for sensing deflection of said jet about said centerline as an indication of acceleration transverse to said centerline;
   a chamber interconnecting said nozzle and said sensing means for accommodating deflection of said jet;
   the difference in density of said first and second fluids being selected to define a desired sensitivity of said accelerometer.

4. The laminar flueric density sensor according to claim 3 wherein said chamber includes vent means on each side of said centerline to be connected to a negative pressure source relative to said nozzle to draw said fluids into said chamber.

5. The laminar flueric density sensor according to claim 3 wherein said sensing means includes a pair of output channels symmetrical about a divider which is on the centerline of said nozzle.

6. The laminar flueric accelerator according to claim 3 wherein said sensing means senses deflection of said jet about said centerline at a fixed acceleration as an indication of the attitude of said centerline.

7. A laminar flueric density sensor comprising:
   a nozzle with a divider for emitting a sample fluid and a reference fluid from a respective side of said divider as a single laminar jet;
   sensing means disposed down stream for sensing deflection of said jet about the nozzle's centerline as an indication of relative density of said sample fluid and said reference fluid; and
   a chamber interconnecting said nozzle and said sensing means for accommodating deflection of said jet, said chamber including vent means for drawing fluid on each side of said centerline to be connected to a negative pressure source to draw said fluids into said chamber.

* * * * *